United States Patent [19]

Marsh et al.

[11] Patent Number: 4,788,042
[45] Date of Patent: Nov. 29, 1988

[54] SYSTEM FOR CONVERSION OF METHANOL TO GASOLINE

[75] Inventors: Susan K. Marsh, East Brunswick; Hartley Owen, Belle Mead; Bernard S. Wright, East Windsor, all of N.J.

[73] Assignee: Mobil Oil Corporation, New York, N.Y.

[21] Appl. No.: 104,617

[22] Filed: Oct. 5, 1987

Related U.S. Application Data

[63] Continuation-in-part of Ser. No. 815,438, Dec. 31, 1985, abandoned.

[51] Int. Cl.[4] .............................................. F08D 7/00
[52] U.S. Cl. .................................... 422/235; 422/234; 585/408; 585/640; 585/469; 585/733; 585/402; 585/403
[58] Field of Search ............... 585/408, 640, 469, 733, 585/402, 403; 482/210, 235, 234

[56] References Cited

U.S. PATENT DOCUMENTS

| | | | |
|---|---|---|---|
| 3,969,426 | 7/1976 | Owen et al. | 585/640 |
| 4,444,988 | 4/1984 | Capsuto et al. | 585/415 |
| 4,456,779 | 6/1984 | Owen et al. | 585/415 |
| 4,456,781 | 6/1984 | Marsh et al. | 585/533 |
| 4,543,435 | 9/1985 | Gould et al. | 585/469 |
| 4,568,786 | 2/1986 | Hsia Chen et al. | 585/513 |
| 4,587,373 | 5/1986 | Hsia | 585/639 |
| 4,665,249 | 5/1987 | Mao et al. | 585/408 |

*Primary Examiner*—Asok Pal
*Attorney, Agent, or Firm*—Alexander J. McKillop; Michael G. Gilman; L. G. Wise

[57] ABSTRACT

A methanol-to-gasoline (MTG) catalytic conversion system in which the conversion is conducted in a fixed bed catalytic reactor. A $C_3$–$C_4$ hydrocarbon diluent is generated from pressurized liquid effluent and recycled to the fixed bed reactor in order to dissipate the heat of reaction.

1 Claim, 1 Drawing Sheet

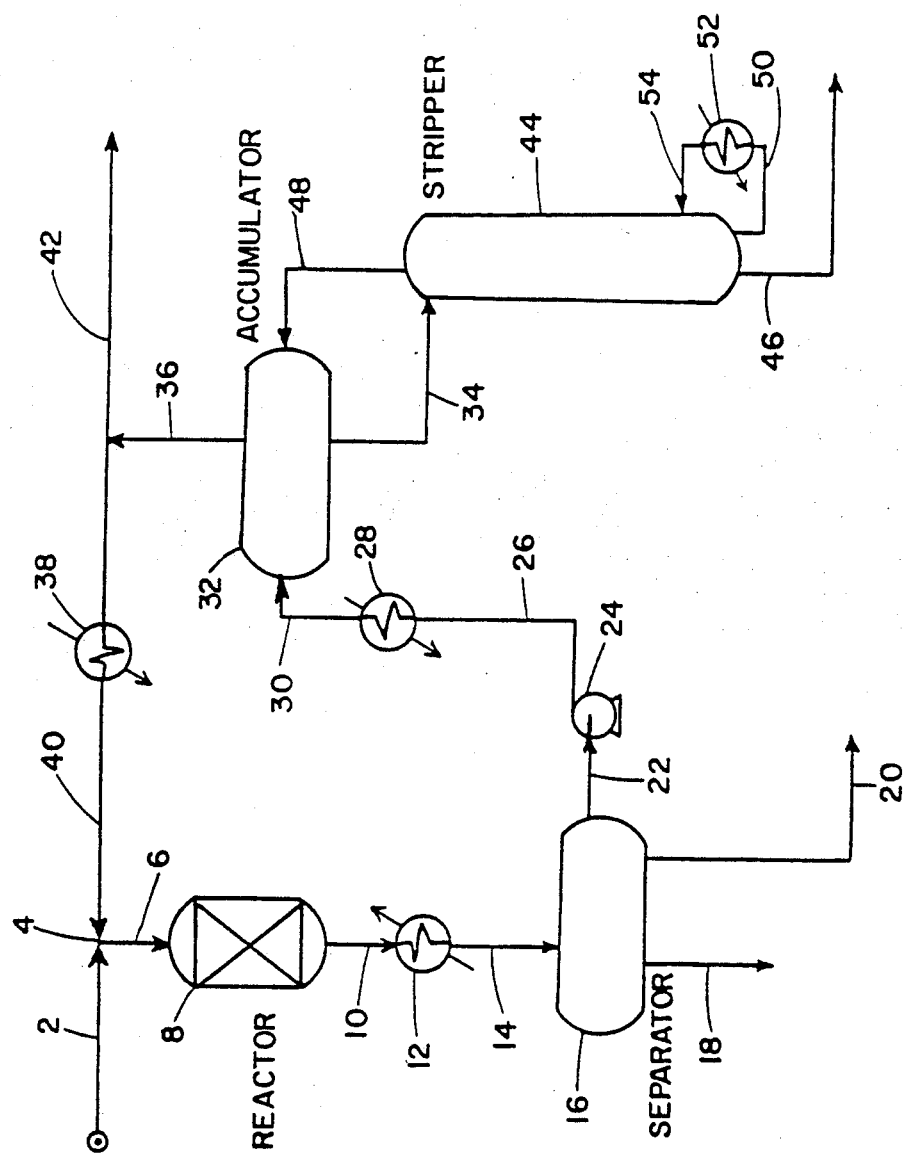

4,788,042

SYSTEM FOR CONVERSION OF METHANOL TO GASOLINE

REFERENCE TO COPENDING APPLICATION

This case is a continuation-in-part of Ser. No. 815,438, filed Dec. 31, 1985, now abandoned.

FIELD OF THE INVENTION

This invention relates to apparatus for converting methanol and other oxygenated organic compounds to gasoline boiling range hydrocarbons. More specifically the invention relates to a system for moderating the temperature rise resulting from the large heat of reaction in a catalytic fixed-bed MTG (methanol to gasoline) reactor.

BACKGROUND OF THE INVENTION

Processes for converting lower oxygenates such as methanol and dimethyl either to hydrocarbons are known and have become of great interest in recent times because they offer an attractive way of producing liquid hydrocarbon fuels, especially gasoline, from sources which are not of liquid petroliferous origin. In particular, they provide a way by which methanol can be converted to gasoline boiling range products in good yields. The methanol, in turn, may be readily obtained from coal by gasification to synthesis gas and conversion of the synthesis gas to methanol by well-established industrial processes. An as alternative, the methanol may be obtained from natural gas by other conventional processes.

The conversion of methanol and other lower aliphatic oxygenates to hydrocarbon products may take place in a fixed bed process as described in U.S. Pat. Nos. 3,998,899; 3,931,349 (Kuo) and 4,035,430. In the fixed bed process, the methanol is usually first subjected to a dehydrating step, using a catalyst such as gamma-alumina, to form an equilibrium mixture of methanol, dimethyl ether (DME) and water. This mixture is then passed at elevated temperature and pressure over a catalyst such as ZSM-5 zeolite for conversion to the hydrocarbon products which are mainly in the range of light gas to gasoline. Water may be removed from the methanol dehydration products prior to further conversion to hydrocarbons and the methanol can be recycled to the dehydration step, as described in U.S. Pat. No. 4,035,430. Removal of the water is desirable because the catalyst may tend to become deactivated by the presence of excess water vapor at the reaction temperatures employed; but this step is not essential.

In the operation of an adiabatic fixed bed process, a major problem is thermal balance. The conversion of the oxygenated feed stream (methanol, DME) to the hydrocarbons is a strongly exothermic reaction liberating approximately 1480 kJ. (1400 Btu) of heat per kilogram of methanol. In an uncontrolled adiabatic reactor this would result in a temperature rise which would lead to extremely fast catalyst aging rates or even to damage to the catalyst. Furthermore, the high temperatures which might occur could cause undesirable products to be produced or the product distribution could be unfavorably changed. It is therefore necessary that some method should be provided to maintain the catalyst bed within desired temperature limits by dissipating the heat of the reaction.

One method is to employ a light gas portion of the hydrocarbon product as recycle, as described in U.S. Pat. No. 3,931,349 (Kuo). Typically, cooled light hydrocarbon gas, rich in methane, ethane, etc., is separated from the gasoline and LPG products, re-compressed and reheated before being mixed with the reactant feedstream entering the bed of conversion catalyst. Although effective in controlling bed temperature, the expense of cooling the recycle gas, compressing it and re-heating it add to the cost of the conversion, indicating that a reduction in recycle ratio would be economically desirable. The recycle ratio can indeed be decreased but only with certain disadvantages. Not only will the temperature rise across the catalyst bed be greater, thereby increasing the aging rate of the catalyst but, in addition, the reactor must be operated at a lower and generally less favorable temperature; the outlet temperature must be lowered in order to protect the catalyst from the increased partial pressure of the water which is consequent upon the lower partial pressure of the recycle gas and the inlet temperature must be lowered even further in order to compensate for the greater temperature rise across the catalyst bed. This is generally undesirable because the octane number of the gasoline product is related to reactor temperature with the higher octane products being produced at the higher temperatures. There is also a minimum reactor inlet temperature that must be maintained for the conversion to proceed and consequently, there is a limit on the extent to which the recycle ratio can be reduced.

A similar proposal is set out in U.S. Pat. No. 4,404,414. The process described in this patent employs a number of fixed bed reaction zones in which oxygenated feedstock is converted to hydrocarbon products by means of contact with a conversion catalyst. The temperature in the reactors is maintained at the desired value by the use of a diluent which is passed through the reactors in sequence before it is completely cooled and separated from the conversion products. The diluent in this case is light hydrocarbon gases which have been separated from the liquid hydrocarbon products and water. Once again, the expense of cooling the recycle gas, compressing it and re-heating it add to the cost of the conversion.

SUMMARY OF THE INVENTION

According to the present invention an oxygenated organic feedstock such as methanol or DME or mixtures thereof is converted to a hydrocarbon product by charging the feedstock to a fixed bed reaction zone in which substantially all oxygenates are converted to hydrocarbon products by contacting with a conversion catalyst. An improved continuous reactor system has been designed for converting methanol and/or dimethylether feedstock to gasoline boiling range hydrocarbons in the presence of a diluent vapor in a fixed bed adiabatic reactor with a solid zeolite catalyst wherein cooled reactor effluent is separated into a byproduct water stream, light hydrocarbon gas stream, and a condensed liquid hydrocarbon stream. The improved technique relates to apparatus, including phase separation means for maintaining effluent phase separation under conditions of pressure and temperature to recover a byproduct water phase, a withdrawn by product vapor phase rich in $C_2-$ hydrocarbons and a condensed liquid hydrocarbon phase comprising a major amount of $C_3+$ hydrocarbons. The equipment also includes means for pumping the condensed liquid phase above reaction zone process pressure; means for heating the condensed liquid stream to vaporize a major amount of $C_3$–$C_4$ hydrocarbons to provide a recycle diluent stream comprising $C_3$–$C_4$ hydrocarbons and a liquid gasoline product stream; means for reheating the $C_3$–$C_4$ recycle diluent stream; and means for combining recycle diluent with feedstock and introducing the feedstock-diluent mixture to the reaction zone at elevated temperature and process pressure.

DRAWINGS

The single FIGURE of the accompanying drawings is a simplified process flowsheet of the present invention.

DETAILED DESCRIPTION

The novel reactor system herein is useful for the conversion of a number of oxygenated organic compounds into hydrocarbon products where the conversion is carried out by an exothermic catalytic reaction. The process is useful for the conversion of aliphatic compounds including lower alcohols such as methanol, ethanol and propanol; ethers, such as dimethylether (DME) and diethyl ether; ketones such as acetone, methylethylketone; aldehydes such as acetaldehyde; esters, such as methyl formate, methyl acetate and ethyl acetate; carboxylic acids, such as acetic acid, butyric acid; and their anhydrides, e.g., acetic anhydride. Examples of conversions of such compounds may be found in U.S. Pat. Nos. 3,907,915, 3,894,107, 3,894,106, 3,894,103, 3,894,104, and 3,894,105 to which reference is made for details of the conversions. The hydrocarbon product in each case will be a hydrocarbon mixture ranging from light gas to heavier fractions ($C_{10+}$) but will generally be concentrated in the gasoline boiling range ($C_5$-220° C.). The MTG process is particularly useful in the catalytic conversion of methanol and its corresponding ether to hydrocarbons in the gasoline boiling range. For convenience, the process will be described below with reference to such a process; although it should be remembered that the principles are applicable to a broader range of conversion.

If methanol is used as the starting material for the process it is preferred to subject it to an initial dehydration step over a catalyst such as gamma-alumina to form an intermediate product comprising dimethyl ether (DME). The DME is then passed to the hydrocarbon step with either complete, partial or no separation of the unreacted methanol and the water produced as a by-product of the dehydration. However, it is not essential to carry out this dehydration even though it is preferred.

The FIGURE shows a simplified schematic flowsheet for the conversion of methanol to gasoline. An equilibrium mixture of methanol, DME, and water is fed via lines 2 and 6 to a fixed bed MTG (methanol to gasoline) catalytic reactor 8. From the reactor 8, the effluent product stream leaves via line 10 to a heat exchanger condenser 12 and is passed as a three-phase mixture via line 14 to a primary phase separator 16. The temperature and pressure of the separator are maintained such that the products are split into three separate streams. The byproduct water is recovered via line 18. The light hydrocarbon gas phase is passed via line 20 to a gas separation zone or may be recovered as fuel gas.

The condensed liquid hydrocarbon stream is passed via line 22 to a pump 24, and then via line 26 to a heat exchange evaporator 28 where said liquid stream is partially vaporized. The partially vaporized stream is conducted via line 30 to an accumulator 32, which acts as a first stage in a fractionating tower. A liquid stream comprising $C_5+$ gasoline range hydrocarbons and dissolved light hydrocarbon exits the accumulator 32 and is passed via line 34 to a gasoline stripping column 44. From the stripping column 44, a stabilized gasoline product leaves via line 46.

The vaporized fraction containing predominantly $C_3$–$C_4$ saturated hydrocarbons is passed from accumulator via line 36 to a heat exchange evaporator 38 and then to a mixing zone 4. In the mixing zone 4, the recycled $C_3$–$C_4$ diluent is combined with the oxygenate feedstock prior to entering the MTG catalytic reactor 8. A small purge stream of LPG is separated from the recycle via line 42.

The feedstock for the fixed bed MTG catalytic reactor can be the effluent from a DME dehydration reactor. In such a case, the effluent is an equilibrium mixture of methanol, water and DME. If desired, complete or partial separation into constituent product stream of water, methanol, and DME may be carried out as described in U.S. Pat. No. 4,035,430 by condensation or fractionation, depending upon the degree of purity desired. Removal of at least the water is desirable because the conversion catalysts used in the fixed bed catalytic reactor usually become deactivated under hydrothermal reaction conditions encountered in the conversion. Although it is not feasible to eliminate the presence of water vapor completely from the conversion, because water is a by-product, the removal of water from the charge will lead to a reduction of the water vapor partial pressure in the conversion reactor and will, accordingly, lead to an increase in the useful life of the catalyst.

The dehydration products are passed to an adiabatic fixed bed MTG reactor under conversion conditions at elevated temperature and pressure. The conversion is preferably catalyzed by a medium pore crystalline zeolite catalyst having acidic functionality.

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing high siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference. The preferred class of catalysts is characterized by a Constraint Index of 1 to 12 and a silica:alumina ratio of at least 12:1 and preferably higher e.g., 20:1 to 70:1, or even higher. Constraint Index of a zeolite is a convenient measure of the extent to which a zeolite provides constrained access to its internal structure for molecules of different sizes. It is therefore, a characteristic of the structure of the zeolite but is measured by a test which relies upon the possession of cracking activity by the zeolite. The sample of zeolite selected for determination of the Constraint Index of a zeolite should therefore represent the structure of the zeolite (manifested by its X-ray diffraction pattern) and have adequate cracking activity for the Index to be determined. If the cracking activity of the selected zeolite is too low, the Constraint Index may be determined by using a zeolite sample of the same structure but higher cracking activity which may be obtained, for example, by using an aluminosilicate zeolite of higher aluminum content. Details of the method of determining Constraint Index and of the values of the Index for typical zeolites are given in U.S. Pat. No. 4,106,218 to which reference is made for such details and other information in this respect.

Preferred zeolites which have the specified values of Constraint Index and silica:alumina ratio include zeolites having a ZSM-5 structure such as ZSM-5, ZSM-11, ZSM-12, ZSM-35, ZSM-38 and ZSM-48, which are described in U.S. Pat. Nos. 3,702,886 (ZSM-5), 3,709,979 (ZSM-11), 3,832,449 (ZSM-12), 4,076,842 (ZSM-23) and 4,016,245 (ZSM-35), 4,046,859 (ZSM-38) and 4,397,827 (ZSM-48), and reference is made to these patents for details of these zeolites, their preparation and properties. Of these zeolites, ZSM-5 is preferred.

The zeolite catalyst used is at least partly in the hydrogen form e.g., HZSM-5; but other cations, e.g., Periodic Groups II–VIII or rare earth cations may also be present. When the zeolites are prepared in the presence of organic cations they may be quite inactive possibly because the intracrystalline free space is occupied by the organic cations from the forming solution. The zeolite may be activated by heating in an inert atmosphere to remove the organic cations e.g., by heating at over 500° C. for 1 hour or more. The hydrogen form can then be obtained by base exchange with ammonium salts followed by calcination e.g. at 500° C. in air. Other cations e.g., metal cations can be introduced by conventional base exchange techniques.

In this invention, a novel method for controlling the exothermic reaction is proposed. Rather than employing a $C_2^-$ recycled light hydrocarbon gas as the diluent, $C_3$–$C_4$ rich (LPG) recycle fraction is used. The LPG recycle may comprise, on a molar basis, about 48% isobutane, about 16% propane, and about 18% n-butane, with a minor amount of olefins. Typically, about 95% of the LPG recycle is $C_3$–$C_5$ saturated hydrocarbons. In a preferred embodiment, the recycle vapor stream comprises a molar majority of $C_3$–$C_4$ saturated hydrocarbons.

A major advantage of employing an LPG recycle stream is that condensed liquid can be repumped economically in order to recycle it back to the fixed bed MTG catalytic reactor. If light hydrocarbon gas is used for the recycle, it must be recompressed at great expense. A large gas recycle compressor usually requires a source of high pressure superheated steam; whereas the $C_3$–$C_4$ recycle design utilizes low pressure steam, demanding much less energy to achieve the process reaction pressure.

The LPG recycle stream is miscible with the gasoline boiling range hydrocarbon material, and it may be separated from the gasoline product prior to being employed as the diluent for temperature moderation in the fixed bed catalytic reaction zone. In this invention an accumulator is used to perform initial separation of the LPG recycle stream from the gasoline boiling range hydrocarbons rather than using a standard debutanizer containing rectifying and stripping sections. The use of an accumulator, which may be considered as the first stage in a fractionating tower, allows for stripping of only a small portion of the total liquid product. Such energy-efficient separation of the LPG recycle material provides an acceptable stream of diluent which has a high heat capacity. Thus, less moles of LPG recycle are needed to moderate the temperature rise due to the exothermic reaction heat than for light gas ($C_2^-$) recycle.

In the preferred embodiment, an effluent stream from the DME dehydration reaction zone is passed to a mixing zone where it is combined with LPG recycle. The combined feedstock and recycle diluent is conducted at a temperature of about 340°–345° C. and a pressure of about 1000–1100 kPa to a fixed bed MTG catalytic reactor.

Reactor conditions will vary depending upon water content of crude methanol feedstock. Table I gives a comparison of the reactor and recycle conditions for gas recycle versus LPG recycle when the feed is methanol containing about 4% by weight water.

Effluent from the fixed bed MTG reaction zone is passed to a heat exchange condenser and then to a separation zone without significant loss of pressure. In the separation zone the effluent stream is partitioned into three streams. Typically, the separator is operated at conditions of about 35°–40° C. (100° F.) and about 700–750 kPa (107 psia). From the separator the liquid hydrocarbon fraction is passed to a pump where it is repressurized to about 1100 kPa to 1400 kPa. From the heat exchange evaporator the partially vaporized fraction is passed to an accumulator. The accumulator is operated at about 90–95° C. (195° F.) and about 1200–1300 kPa (186 psia). Conditions for the liquid product distillation tower are given in Table II.

From the accumulator a vaporized fraction containing a major amount of $C_3$–$C_4$ saturated hydrocarbons (LPG) is passed to a zone where it is separated from LPG make. The purified LPG fraction is then conducted to a heat exchange evaporator where it is brought to a temperature of about 335° C. (636° F.) prior to mixing with feedstock.

Referring to Table III, a comparison is made between oxygenate conversion designs employing a light gas recycle as taught in the prior art and an LPG recycle as presently disclosed. Preheating the LPG recycle stream prior to mixing with the oxygenate feedstream is more energy intensive than preheating the light gas recycle stream by an amount of 32 meta watts per kilotonne methanol feed per day. However, the present process of recycling a liquid LPG stream eliminates the use of a compressor, allowing for a savings in total heat input requirement of about 2 mega watts per kilotonne methanol feed per day.

Gasoline yield is increased in the present process because unconverted $C_3$–$C_4$ olefins retained in the LPG recycle stream are upgraded in the catalytic oxygenate conversion reactor to gasoline range hydrocarbons. An increase of about 1% gasoline yields is observed.

Table IV is a comparison of cooling water requirements between an oxygenate conversion design employing a light gas recycle to a conversion zone and a design employing an LPG recycle to a conversion zone, as is presently disclosed. Although the amount of energy necessary to cool reactor effluent in the LPG recycle design is somewhat greater than in the light gas recycle design, the overall cooling water requirement is more energy intensive in the light gas recycle design.

As indicated in Tables III and IV, the present process of recycling LPG to an oxygenate conversion reactor is less energy intensive than a light gas recycle process. In the present process the high pressure steam requirement is eliminated, low pressure steam is efficiently employed, steam usage in the gas plant is reduced, more energy is recovered from the reactor effluent, and there is no cooling water requirement for the turbine drive associated with a compressor.

There is also an equipment savings when practicing the present process. Capital investment is reduced because an expensive recycle gas compressor is not necessary. This also improves unit reliability, as a relatively inexpensive second LPG recycle pump can be added to the unit as a spare.

The invention is illustrated in the following examples.

EXAMPLE 1

A crude methanol feed containing 4% weight water is charged to a fixed bed downflow MTG catalytic reactor at a temperature of about 345° C. (650° F.) and a pressure of 1060 kPa (154 psia). The catalyst employed is HZSM-5 in a fixed bed of 2.44 meters (8 ft). After complete chemical conversion of the oxygenates to hydrocarbons, an effluent stream exits the reactor at a temperature of about 410° C. (775° F.) and is passed to a heat exchange condenser where the temperature is reduced to about 35°–40° C. (100° F.) to condense the major amount of $C_3+$ hydrocarbons.

From the heat exchange condenser the effluent is conducted to a primary phase separator where it is split into a water stream, a light hydrocarbon gas stream, and a liquid hydrocarbon stream. The byproduct water is recovered, the light hydrocarbon gas fraction is sent to an offsite LPG recovery unit, and the liquid hydrocarbon stream is repressurized by pumping and sent to a heat exchange evaporator.

In the heat exchange evaporator the liquid hydrocarbon stream is partially vaporized to provide a $C_3$–$C_4$ rich recycle stream at about 90° C. (194° F.) and a pressure of about 1280 kPa (186 psia). From the accumulator bottom a liquid hydrocarbon stream is passed to a product gasoline stripping tower where it undergoes conversion to a stabilized gasoline product. The gasoline product can be treated to strip $C_4-$ components for combining with the recycle diluent stream. The product tower operates at an overhead temperature of about 90° C. (195° F.) and a bottom temperature of about 190° C. (370° F.), and there are twenty trays in the tower.

From the heat exchange evaporator the recycle $C_3$–$C_4$ hydrocarbon stream is heated further and passed to a mixing zone where it is combined with a methanol feedstock at a temperature of about 345° C. (650° F.) and a pressure of about 1100 kPa (154 psia). The resulting mixture is then conducted to the fixed bed MTG catalytic reactor.

EXAMPLE 2

The procedure of Example 1 is repeated except for the use of crude methanol (MeOH) containing 17 wt % water.

TABLE I
System Operating Conditions for Crude MeOH Feed With 4 wt. % $H_2O$

| | Light Gas Recycle | $C_3$–$C_4$ (LPG) Recycle |
|---|---|---|
| Conversion Reactor Conditions | | |
| Inlet Temperature, °C. | 341 (646° F.) | 343 (650° F.) |
| Outlet Temperature, °C. | 416 (781° F.) | 412 (775° F.) |
| Inlet Pressure, kPa | 1793 (260 psia) | 1062 (154 psia) |
| Bed Depth, Meters | 2.44 (8 ft.) | 2.44 (8 ft.) |
| Overall Reactor P, kPa | 220 (32 psia) | 140 (20 psia) |
| MeOH Equivalent Pressure, kPa (reactor inlet) | 205 (29.8 psia) | 231 (33.5 psia) |

TABLE I-continued
System Operating Conditions for Crude MeOH Feed With 4 wt. % $H_2O$

| | Light Gas Recycle | $C_3$–$C_4$ (LPG) Recycle |
|---|---|---|
| Separator Pressure, kPa Recycle | 1386 (201 psia) | 738 (107 psia) |
| Molar Ratio to Methanol Equivalent | 7.63 | 3.5 |
| Mol Wt. | 27.2 | 56.6 |
| MPH Aromatics per KT/Day MEOH (pure) feed | 11.8 | 18.2 |

TABLE II
Product Distillation Tower Specifications (based on kilotonnes per day methanol feed containing 4 wt. % $H_2O$)

| | |
|---|---|
| Trays (Theoretical) | 20 |
| Reboiler Duty (Mega Watts) | 3.0 |
| Overhead Temperature, °C. | 91 (195° F.) |
| Bottom Temperature, °C. | 188 (371° F.) |
| Pressure, kPa at Accumulator | 1282 (186 psia) |

TABLE III
A Comparison of Principal Heat Balance Items in MTG Designs (based on kilonnes per day methanol feed containing 4 wt. % water)

| | Light Gas Recycle (Mega watts) | LPG Recycle (Mega watts) |
|---|---|---|
| Feed Preheat | | |
| Methanol feed | 20 | 20 |
| Recycle stream | 44 | 76 |
| Reactor Effluent | | |
| Feed and recycle preheat | (64) | (87) |
| Steam generation (4240 kPa) | (4) | (2) |
| Gas Plant | 4.3 | 3.7 |
| Steam usage (2861 kPa) Compressor | 12.4 | — |
| Superheated steam (149° C., 1044 kPa) | | |
| Total Heat Input Requirement | 12.7 | 10.7 |

TABLE IV
A Comparison of Cooling Water Requirements in MTG Designs (based on kilotonnes per day methanol feed containing 4 wt. % water)

| | Light Gas Recycle (Mega watts) | LPG Recycle (Mega watts) |
|---|---|---|
| Reactor Effluent Cooling | 24.3 | 30.3 |
| Condensing for Turbine drive | 8.7 | — |
| Gas plant | 4.3 | 5.0 |
| Total Cooling Water Requirement | 37.3 | 35.3 |

We claim:

1. An apparatus for producing gasoline boiling range hydrocarbons from $C_1$ to $C_3$ oxygenates comprising:
   (a) a fixed bed reaction zone containing a crystalline zeolite catalyst;
   (b) means for transporting the reactor effluent from a reaction zone to a separation zone;
   (c) phase separator means wherein the reactor effluent is split into a gas stream, a water stream, and a liquid hydrocarbon stream;
   (d) means for transporting the liquid hydrocarbon stream to a heat exchange evaporator;

(e) a heat exchange evaporator wherein the liquid hydrocarbon stream is partially vaporized;

(f) means for transporting said partially vaporized stream to an accumulator;

(g) an accumulator operatively connected as the first stage of a fractionating column wherein a vapor phase comprising $C_3$–$C_4$ saturated hydrocarbons is separated from a liquid phase;

(h) means for passing said liquid phase to a gasoline stripping zone;

(i) a gasoline stripping zone wherein a stabilized gasoline product is prepared;

(j) means for conducting said vapor phase from (g) to a further heat exchange evaporator;

(k) a heat exchange evaporator wherein said vapor phase is heated to a temperature sufficient for entrance into a fixed bed reaction zone;

(l) means for passing said heated vapor phase to a mixing zone;

(m) a mixing zone wherein said heated vapor phase comprising $C_3$–$C_4$ saturated hydrocarbons is combined with an oxygenate feedstock; and (n) means for passing said mixture to the fixed bed reaction zone of step (a).

* * * * *